(12) United States Patent
Bahar et al.

(10) Patent No.: US 10,191,069 B2
(45) Date of Patent: Jan. 29, 2019

(54) ACCURATE ASSAY MEASUREMENT OF HYDROPHOBIC HAPTENIC ANALYTES

(71) Applicant: Siemens Healthcare Diagnostics Inc., Tarrytown, NY (US)

(72) Inventors: Izak Bahar, Hockessin (DE); Tie Q. Wei, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 15/536,308

(22) PCT Filed: Dec. 11, 2015

(86) PCT No.: PCT/US2015/065253
§ 371 (c)(1),
(2) Date: Jun. 15, 2017

(87) PCT Pub. No.: WO2016/100117
PCT Pub. Date: Jun. 23, 2016

(65) Prior Publication Data
US 2017/0356922 A1   Dec. 14, 2017

Related U.S. Application Data (60) Provisional application No. 62/093,105, filed on Dec. 17, 2014.

(51) Int. Cl.
| | | |
|---|---|---|
| *G01N 33/82* | (2006.01) | |
| *G01N 33/53* | (2006.01) | |
| *G01N 33/92* | (2006.01) | |
| *G06F 19/00* | (2018.01) | |

(52) U.S. Cl.
CPC ......... *G01N 33/82* (2013.01); *G01N 33/5308* (2013.01); *G01N 33/92* (2013.01); *G06F 19/701* (2013.01)

(58) Field of Classification Search
CPC .... G01N 33/82; G01N 33/92; G01N 33/5308; G06F 19/701
See application file for complete search history.

(56) References Cited

U.S. PATENT DOCUMENTS

| | | |
|---|---|---|
| 2007/0166762 A1 | 7/2007 | Leonard et al. |
| 2010/0068725 A1 | 3/2010 | Armbruster et al. |
| 2013/0084592 A1 | 4/2013 | Seiple |
| 2014/0138261 A1 | 5/2014 | Colas |
| 2014/0242615 A1 | 8/2014 | Wei et al. |
| 2017/0114012 A1 | 4/2017 | Teng et al. |
| 2017/0121426 A1 | 5/2017 | Sharma et al. |
| 2017/0153254 A1 | 6/2017 | Wei et al. |

FOREIGN PATENT DOCUMENTS

WO    2015200178 A1   12/2015

OTHER PUBLICATIONS

European Search Report and Written Opinion of European Application No. 158707612 dated Sep. 7, 2017.
International Search Report and Written Opinion of International Application No. PCT/US2015/065253 dated Feb. 23, 2016.

*Primary Examiner* — Shafiqul Haq
(74) *Attorney, Agent, or Firm* — Cynthia G. Tymeson (57) ABSTRACT

Methods are disclosed for determining an actual concentration of a hydrophobic haptenic analyte in an unknown sample suspected of containing the hydrophobic haptenic analyte, wherein the unknown sample is suspected of containing an interfering substance. A first assay method is conducted on an unknown sample to obtain a measured concentration of the hydrophobic haptenic analyte in the unknown sample. A second assay method is conducted on the unknown sample to obtain a concentration of the interfering substance in the unknown sample. A predetermined correction formula that utilizes the measured concentration of the hydrophobic haptenic analyte and the measured concentration of the interfering substance obtained in step (a) is applied to determine an actual concentration of the hydrophobic haptenic analyte in the unknown sample.

13 Claims, 4 Drawing Sheets

ACCURATE ASSAY MEASUREMENT OF HYDROPHOBIC HAPTENIC ANALYTES

The subject application claims benefit under 35 USC § 119(e) of U.S. Provisional Application No. 62/093,105, filed Dec. 17, 2014. The entire contents of the above-referenced patent application are hereby expressly incorporated herein by reference.

BACKGROUND

The invention relates to methods for the determination of the concentration of an analyte in a sample suspected of containing the analyte. More particularly, the invention relates to reducing the effect of interfering substances on measurements conducted during the above methods for the determination of the concentration of an analyte in a sample.

Hydrophobic compounds such as, for example, drugs, vitamins such as, e.g., vitamin D and vitamin B12, and hapten hormones, are often found in the hydrophobic core of lipoproteins, whose surrogate analyte marker is cholesterol, which resides in all lipoproteins including low density lipoprotein (LDL), very low density lipoprotein (VLDL), intermediate density lipoprotein (IDL), high density lipoprotein (HDL) and chylomicrons.

As indicated above, vitamin D is one such hydrophobic compound. After formation of vitamin D by UV Light, it is transported by lipoproteins and vitamin D binding proteins (VDBP) in the blood. In assays for vitamin D where vitamin D is not extracted using an organic solvent such as, for example, an alcohol, vitamin D is released from VDBP using a suitable releasing agent. However, vitamin D molecules in the core of lipoproteins are left in the core of the lipoproteins and are untouched for the most part. Extraction assays are laborious and, as mentioned above, involve the use of organic solvents on a sample. Therefore, most immunoassays for vitamin D or other hydrophobic compounds are negatively impacted by one or more interfering substances such as, for example, cholesterol and lipoproteins in a sample because vitamin D molecules that are not released from the interfering substances such as, for example, the core of lipoproteins, are not accessible to an antibody used in an immunoassay. The actual amount of vitamin D in a sample may not be accurately determined and the amount of vitamin D observed in an immunoassay may be falsely elevated or suppressed.

Assessing vitamin D levels in biological samples is important since vitamin D deficiency is related to a number of disorders in mammals. There is a continuing need to develop fast and accurate diagnostic methods to measure a level of a hydrophobic haptenic analyte in a sample taken from a patient. The methods should be fully automatable and be accurate even when conducted on samples having various interfering substances. The assay methods should provide an accurate measurement of the amount of the hydrophobic haptenic analyte in the sample while minimizing inaccuracies resulting from interfering substances present in the sample.

SUMMARY

Some examples in accordance with the principles described herein are directed to methods of determining an actual concentration of a hydrophobic haptenic analyte in an unknown sample suspected of containing the hydrophobic haptenic analyte, wherein the unknown sample is suspected of containing an interfering substance. A first assay method is conducted on an unknown sample to obtain a measured concentration of the hydrophobic haptenic analyte in the unknown sample. A second assay method is conducted on the unknown sample to obtain a concentration of the interfering substance in the unknown sample. A predetermined correction formula that utilizes the measured concentration of the hydrophobic haptenic analyte and the measured concentration of the interfering substance obtained in step (a) is applied to determine an actual concentration of the hydrophobic haptenic analyte in the unknown sample. The correction formula is predetermined by a method that comprises: (i) measuring a concentration of the hydrophobic haptenic analyte for at least two different samples using the first assay method and measuring the concentration of the hydrophobic haptenic analyte for the at least two different samples using a reference method wherein the at least two different samples also comprise the interfering substance, (ii) determining a bias between the first assay method and the reference method wherein the bias is the difference between the concentration of the hydrophobic haptenic analyte determined by the reference method and the first assay method for each different sample, (iii) measuring a concentration of the interfering substance for each of the at least two different samples, and (iv) determining the correction formula by conducting a regression analysis using the bias and the concentration of the interfering substance in each of the at least two different samples.

Some examples in accordance with the principles described herein are directed to methods of determining an actual concentration of a vitamin D analyte in an unknown sample suspected of containing the vitamin D analyte, wherein the unknown sample is suspected of containing cholesterol. A first assay method on an unknown sample is conducted to obtain a measured concentration of the vitamin D analyte in the unknown sample. A second assay method is conducted on the unknown sample to obtain a concentration of cholesterol. A predetermined correction formula that utilizes the measured concentration of the vitamin D analyte and the measured concentration of cholesterol obtained in step (a) is applied to determine an actual concentration of the vitamin D analyte in the unknown sample. The correction formula is predetermined by a method that comprises: (i) measuring a concentration of the vitamin D analyte for at least two different samples using the first assay method and measuring the concentration of the vitamin D analyte for each of the at least two different samples using a reference method wherein the samples also comprise cholesterol, (ii) determining a bias between the first assay method and the reference method wherein the bias is the difference between the concentration of the vitamin D analyte determined by the reference method and the assay method for each of the at least two different samples, (iii) measuring a concentration of cholesterol in each of the at least two different samples, and (iv) determining the correction formula by conducting a regression analysis using the bias and the concentration of cholesterol in each of the at least two different samples.

BRIEF DESCRIPTION OF DRAWINGS

The drawings provided herein are not to scale and are provided for the purpose of facilitating the understanding of certain examples in accordance with the principles described herein and are provided by way of illustration and not limitation on the scope of the appended claims.

DETAILED DESCRIPTION OF SPECIFIC EMBODIMENTS

General Discussion

Examples of methods in accordance with the principles described herein provide for accurate measurement of a hydrophobic haptenic analyte in a sample taken from a host where the sample contains one or more interfering substances that impact the ability to accurately detect the hydrophobic haptenic analyte. In examples of methods in accordance with the principles described herein, measured concentrations for hydrophobic haptenic analytes are corrected by measuring the concentration of hydrophobic haptenic analyte in a portion of an unknown sample using an assay method and measuring the concentration of an interfering substance in another portion of the unknown sample using another, usually different, assay method and applying a predetermined correction formula that utilizes both of the above measurements to obtain an accurate measurement of the hydrophobic haptenic analyte in the unknown sample. In some examples, measurement of the concentration of the interfering substance is conducted as part of a panel of tests that also includes measurement of the hydrophobic haptenic analyte.

The correction formula is predetermined by a method that comprises: (i) measuring a concentration of the hydrophobic haptenic analyte for at least two different samples using the first assay method and measuring the concentration of the hydrophobic haptenic analyte for each of the two different samples using a reference method wherein the samples also comprise the interfering substance, (ii) determining a bias between the first assay method and the reference method wherein the bias is the difference between the concentration of the hydrophobic haptenic analyte determined by the reference method and the first assay method for each of the two different samples, (iii) measuring a concentration of the interfering substance in each of the two different samples, and (iv) determining the correction formula by conducting a regression analysis using the bias and the concentration of the interfering substance for each of the at least two different samples.

The present inventor found that using a correction formula as discussed above results in a more accurate determination of a hydrophobic haptenic analyte whether the interfering substances cause the assay measurement to be too high or too low in the absence of a correction formula.

The phrase "hydrophobic haptenic analyte" refers to an analyte that has a molecular weight less than about 2,500, or less than about 2,000, or less than about 1,500, or less than about 1,000, or less than about 500 and is in the molecular weight range of about 100 to about 2,500, or about 300 to about 2,500, or about 300 to about 2,000, or about 300 to about 1,500, or about 300 to about 1,000, or about 500 to about 2,500, or about 500 to about 2,000, or about 500 to about 1,500, or about 500 to about 1,000, for example. The hydrophobic haptenic analyte is fat soluble, which means that the hydrophobic haptenic analyte is soluble in one or more of fats, oils, and lipids, for example.

In some examples, the hydrophobic haptenic analytes include, but are not limited to, vitamins, drugs of abuse, therapeutic drugs, and steroid hormones, for example. Vitamins include, but are not limited to, vitamin D, vitamin B12, vitamin E and vitamin K, for example. Steroid hormones include, by way of illustration and not limitation, progestogens, estrogens, androgens, glucosteroids, mineralocorticoids, and secosteroids, for example. In some examples in accordance with the principles described herein, the hydrophobic haptenic analyte is vitamin D, for example.

As used herein, the term "vitamin D" refers to a group of fat-soluble secosteroids and includes, for example, one or more of 25-hydroxycholecalciferol (also referred to as calcidiol, calcifediol, 25-hydroxycholecalciferol, or 25-hydroxyvitamin D (abbreviated 25(OH)D) including 25-hydroxyvitamin $D_3$ and 25-hydroxyvitamin $D_2$; calcidiol; 1,25-dihydroxyvitamin $D_3$ (calcitriol; 1,25(OH)$_2$D$_3$); 1,25-dihydroxy vitamin $D_4$; 1,25-dihydroxy vitamin $D_5$; and 1,25-dihydroxy vitamin $D_6$; including one or more metabolites of all of the above.

The sample to be analyzed is one that is suspected of containing a hydrophobic haptenic analyte and one or more interfering substances. The samples may be biological samples or non-biological samples. Biological samples may be from a mammalian subject or a non-mammalian subject. Mammalian subjects may be, e.g., humans or other animal species. "Non-biological samples" are those that do not relate to a biological material and include, for example, soil samples, waste streams, water samples, air samples, samples of gases other than air, and mineral samples. The phrase "biological sample" refers to any biological material such as, for example, body fluid, body tissue, body compounds and culture media. The sample may be a solid, semi-solid or a fluid (a liquid or a gas) from any source. In some embodiments the sample may be a body excretion, a body aspirant, a body excisant or a body extractant. The body is usually that of a mammal and in some embodiments the body is a human body. Body excretions are those substances that are excreted from a body (although they also may be obtained by excision or extraction) such as, for example, urine, feces, stool, vaginal mucus, semen, tears, breath, sweat, blister fluid and inflammatory exudates. Body excisants are those materials that are excised from a body such as, for example, skin, hair and tissue samples including biopsies from organs and other body parts. Body aspirants are those materials that are aspirated from a body such as, for example, mucus, saliva and sputum. Body extractants are those materials that are extracted from a body such as, for example, whole blood, plasma, serum, spinal fluid, cerebral spinal fluid, lymphatic fluid, synovial fluid and peritoneal fluid. In some examples the sample is whole blood, plasma or serum.

The phrase "interfering substances" refers to one or more compounds that interact with a hydrophobic haptenic analyte and render the hydrophobic haptenic analyte unavailable for binding to a binding partner such as an antibody for the hydrophobic haptenic analyte that is used in an assay for the determination of the hydrophobic haptenic analyte. Such interfering substances include, but are not limited to, cholesterol, which resides in all lipoproteins including LDL, VLDL, IDL, HDL and chylomicrons, for example.

Determination of Correction Formula

Examples in accordance with the principles described herein have particular application to assays for hydrophobic haptenic analytes where interfering substances impact the accuracy of the measurement. As mentioned above, a predetermined correction formula is employed to correct an assay measurement for an inaccurate result due to the presence of one or more interfering substances in the sample that is tested. In examples in accordance with the principles described herein, a method for predetermining a correction formula comprises measuring a concentration of the hydrophobic haptenic analyte for at least two different samples using a first assay method and measuring the concentration of the hydrophobic haptenic analyte using a reference method for each of the at least two different samples wherein each of the samples also comprises the interfering substance.

A predetermined correction formula is determined by, for example, a manufacturer or a developer, for each assay that may be used to determine a concentration of a hydrophobic haptenic analyte in an unknown sample from a host. Once predetermined, the correction formula may be disseminated by, for example, inclusion with instructions for an assay, to a user such as, for example, a laboratory, for use in the determination of concentrations of hydrophobic haptenic analyte in unknown samples. The predetermined correction formula is simply applied by the user to the assay results obtained for the subsequent analysis of unknown samples in order to calculate an accurate concentration of a hydrophobic haptenic analyte in the unknown samples.

In predetermining the correction formula, the number of different samples containing the hydrophobic haptenic analyte that are subjected to the first assay method is at least two, or at least three, or at least four, or at least five, or at least six. In some examples, the number of different samples containing the hydrophobic haptenic analyte that may be employed is between 2 and 20, or between 2 and 15, or between 2 and 14, or between 2 and 13, or between 2 and 12, or between 2 and 11, or between 2 and 10, or between 3 and 20, or between 3 and 15, or between 3 and 14, or between 3 and 13, or between 3 and 12, or between 3 and 11, or between 3 and 10, or between 4 and 20, or between 4 and 15, or between 4 and 12, or between 4 and 10, or between 5 and 20, or between 5 and 15, or between 5 and 12, or between 5 and 10, or between 6 and 15, or between 6 and 14, or between 6 and 13, or between 6 and 12, or between 7 and 15, or between 7 and 14, or between 7 and 13, or between 7 and 12, or between 8 and 20, or between 8 and 15, or between 8 and 12, for example.

In some examples, the concentrations of hydrophobic haptenic analytes employed span the expected concentration range of the hydrophobic haptenic analytes in unknown samples to be analyzed. The concentration of the hydrophobic haptenic analyte that may be assayed generally varies from about $10^{-5}$ to about $10^{-17}$ M, or from about $10^{-6}$ to about $10^{-14}$ M, or from about $10^{-8}$ M to about $10^{-10}$ M, for example. The concentration of the interfering substance in each of the samples may vary between about 10 mg/dL to about 1,000 mg/dL, or about 50 mg/dL to about 1,000 mg/dL, or about 100 mg/dL to about 1,000 mg/dL, or about 200 mg/dL to about 1,000 mg/dL, or about 300 mg/dL to about 1,000 mg/dL, or about 500 mg/dL to about 1,000 mg/dL, or about 10 mg/dL to about 500 mg/dL, or about 50 mg/dL to about 500 mg/dL, or about 100 mg/dL to about 500 mg/dL, or about 200 mg/dL to about 500 mg/dL, or about 300 mg/dL to about 500 mg/dL, for example.

The first assay method employed in predetermining a correction formula is the assay method that would subsequently be employed for measuring samples suspected of containing a hydrophobic haptenic analyte, that is, unknown samples. Any assay method may be employed as the first assay method. In some examples, the first assay method comprises adding reagents for determining the concentration of the hydrophobic analyte in the sample to a medium comprising the sample wherein the reagents comprise at least one binding partner for the hydrophobic analyte, and incubating the medium under conditions for binding of the hydrophobic analyte to the binding partner for the hydrophobic analyte. The binding results in complexes comprising the binding partner for the analyte and the analyte or an analyte analog. The amount of such complexes are measured and related to the amount of the analyte in the sample.

The phrase "binding partner" refers to a molecule that is a member of a specific binding pair, which is one of two different molecules that specifically binds to and is thereby defined as complementary with the other molecule. For example, one member of the specific binding pair may have an area on the surface or in a cavity that specifically binds to a particular spatial and polar organization of the other member of the specific binding pair. The binding partner may be, by way of illustration and not limitation, an antibody or an aptamer (e.g., nucleic acid aptamer or peptide aptamer), for example.

Assays that employ an antibody as one reagent are referred to as immunoassays. The phrase "antibody for the analyte" refers to an antibody that binds specifically to an analyte (and in some example to closely related structural analogs of the analyte such as metabolites of the analyte) and does not bind to any significant degree to other substances that would distort the analysis for the analyte. Accordingly, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules.

In general, an assay employed as a first assay method for predetermining a correction formula in accordance with the principles described herein is conducted by combining in an assay medium a sample containing the hydrophobic haptenic analyte and an antibody for the hydrophobic haptenic analyte. The antibody may be employed in a free or a conjugated mode. A conjugated antibody is an antibody that is bound to a support or a label, or to a combination of a support and a label, for example. The nature of other reagents employed is dependent on the particular type of assay to be performed. The combination in the medium is subjected to conditions for binding of the analyte or an analyte analog to the antibody to form a complex. The amount of the complex is measured where the amount of the complex is related to the amount of analyte in the medium.

An "analyte analog" is a modified analyte that competes with the analyte for binding to a receptor such as an antibody for the analyte. The modification provides means to join an analyte analog to another molecule. The analyte analog will usually differ from the analyte by more than replacement of a hydrogen with a bond which links the analyte analog to a hub or label, but need not. The analyte analog may be, for example, the analyte conjugated to another molecule such as, for example, a label or a support, through a bond or a linking group, for example.

An assay can be performed either without separation (homogeneous) or with separation (heterogeneous) of any of the assay components or products. Heterogeneous assays usually involve one or more separation steps and can be competitive or non-competitive. Immunoassays may involve labeled or non-labeled reagents. Immunoassays involving non-labeled reagents usually comprise the formation of relatively large complexes involving one or more antibodies prepared from immunogenic conjugates in accordance with the principles described herein. Such assays include, for example, immunoprecipitin and agglutination methods and corresponding light scattering techniques such as, e.g., nephelometry and turbidimetry, for the detection of antibody complexes. Labeled immunoassays include, but are not limited to, chemiluminescence immunoassays, enzyme immunoassays, fluorescence polarization immunoassays, radioimmunoassays, inhibition assays, induced luminescence assays, and fluorescent oxygen channeling assays, for example.

One general group of immunoassays includes immunoassays using a limited concentration of one of the reagents. Another group of immunoassays involves the use of an excess of one or more of the principal reagents. Another group of immunoassays is separation-free homogeneous assays in which a labeled reagent modulates the label signal upon binding of an analyte or analyte analog to an antibody in the sample.

As mentioned above, the assays can be performed either without separation (homogeneous) or with separation (heterogeneous) of any of the assay components or products. Homogeneous immunoassays are exemplified by the EMIT® assay (Siemens Healthcare Diagnostics Inc., Deerfield, Ill.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and enzyme immunoassays such as the enzyme linked immunosorbent assay ("ELISA"). Exemplary of heterogeneous assays are the radioimmunoassay, disclosed in Yalow, et al., J. Clin. Invest. 39:1157 (1960). The relevant portions of the above disclosures are all incorporated herein by reference.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), and particle enhanced turbidimetric immunoassay ("PETIA"); for example.

Other assays include the sol particle immunoassay ("SPIA"), the disperse dye immunoassay ("DIA"); the metalloimmunoassay ("MIA"); the enzyme membrane immunoassays ("EMIA"); and luminoimmunoassays ("LIA"); for example. Other types of assays include immunosensor assays involving the monitoring of the changes in the optical, acoustic and electrical properties of a compound upon the binding to an antibody. Such assays include, for example, optical immunosensor assays, acoustic immunosensor assays, semiconductor immunosensor assays, electrochemical transducer immunosensor assays, potentiometric immunosensor assays, and amperometric electrode assays.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In an example of a competitive heterogeneous assay, a support having an antibody for an analyte bound thereto is contacted with a medium containing the sample suspected of containing the analyte and a labeled analyte analog. Analyte in the sample competes with the analyte analog, which may be bearing a detectable label, for binding to the antibody for the analyte. After separating the support and the medium, the label activity of the support or the medium is determined by conventional techniques and is related to the amount of analyte in the sample.

The medium employed in an assay method for predetermining a correction formula in accordance with the principles described herein is an aqueous buffered medium at a moderate pH, generally that which provides optimum assay sensitivity. The aqueous medium may be solely water or may include from 0.1 to about 40 volume percent of a cosolvent. The pH for the medium will be in the range of about 4 to about 11, or in the range of about 5 to about 10, or in the range of about 6.5 to about 9.5. The pH will usually be a compromise between optimum binding of the binding members of any specific binding pairs, the pH optimum for other reagents of the assay such as members of the signal producing system, and so forth. Various buffers may be used to achieve the desired pH and maintain the pH during the assay. Illustrative buffers include borate, phosphate, carbonate, tris, barbital, PIPES, HEPES, MES, ACES, MOPS, BICINE, and the like. The particular buffer employed is not critical, but in an individual assay one or another buffer may be preferred.

Various ancillary materials may be employed in the assay methods. For example, in addition to buffers the medium may comprise stabilizers for the medium and for the reagents employed. In some embodiments, in addition to these additives, proteins may be included, such as albumins; organic solvents such as formamide; quaternary ammonium salts; polyanions such as dextran sulfate; binding enhancers, e.g., polyalkylene glycols; polysaccharides such as dextran, trehalose, or the like. The medium may also comprise agents for preventing the formation of blood clots. Such agents are well known in the art and include, for example, EDTA, EGTA, citrate, heparin, and the like. The medium may also comprise one or more preservatives as are known in the art such as, for example, sodium azide, neomycin sulfate, PROCLIN® 300, Streptomycin, and the like. Any of the above materials, if employed, is present in a concentration or amount sufficient to achieve the desired effect or function.

Depending on the nature of the assay employed, the medium may comprise one or more components such as, for example, other members of a signal producing system of which the label is a part.

The signal producing system may have one or more components, at least one component being a label. The signal producing system generates a signal that relates to the presence of a hydrophobic haptenic analyte in a sample. The signal producing system includes all of the reagents required to produce a measurable signal. Other components of the signal producing system may be included in a developer solution and can include, but are not limited to, substrates, enhancers, activators, chemiluminescent compounds, cofactors, inhibitors, scavengers, metal ions, and specific binding substances required for binding of signal generating substances, for example. Other components of the signal producing system may be coenzymes, substances that react with enzymic products, other enzymes and catalysts, for example. The signal producing system provides a signal detectable by external means, by use of electromagnetic radiation, desirably by visual examination. Exemplary signal-producing systems are described in U.S. Pat. No. 5,508,178, the relevant disclosure of which is incorporated herein by reference.

The term "label" includes poly(amino acid) labels and non-poly(amino acid) labels. The term "poly(amino acid) label moieties" includes labels that are proteins such as, but not limited to, enzymes, antibodies, peptides, and immunogens, for example. The term "non-poly(amino acid) labels" includes those labels that are not proteins. The non-poly (amino acid) label is capable of being detected directly or is detectable through a reaction that produces a detectable signal. The non-poly(amino acid) label can be isotopic or non-isotopic and can be, by way of illustration and not limitation, a radioisotope, a luminescent compound (which includes, but is not limited to acridinium esters, fluorescent compounds and chemiluminescent compounds, for example), a polynucleotide coding for a catalyst, a promoter, a dye, a coenzyme, an enzyme substrate, a radioactive group, and an amplifiable polynucleotide sequence, for example. In some example, the non-poly(amino acid) labels are radioisotopic, luminescent (such as, e.g., acridinium esters), particulate (such as, e.g., magnetic particles that can be separated bound from un-bound, latex particles that can be measured by turbidity and nephelometry, and chemiluminescence beads (e.g., LOCI chemibeads), for example.

Some known assays utilize a signal producing system (sps) that employs first and second sps members. The sps members may be related in that activation of one member of the sps produces a product such as, e.g., light, which results in activation of another member of the sps.

In some embodiments of known assays, the sps members comprise a sensitizer such as, for example, a photosensitizer, and a chemiluminescent composition where activation of the sensitizer results in a product that activates the chemiluminescent composition. The second sps member usually generates a detectable signal that relates to the amount of bound and/or unbound sps member, i.e., the amount of sps member bound or not bound to the analyte being detected or to an agent that reflects the amount of the analyte to be detected. In some examples in accordance with the principles described herein, one of either the sensitizer reagent or the chemiluminescent reagent is a conjugate reagent prepared in accordance with the principles described herein. Examples of photosensitizers and chemiluminescent reagents that may be utilized are those set forth in U.S. Pat. Nos. 5,340,716 and 6,251,581, the relevant disclosures of which are incorporated herein by reference.

In a particular example by way of illustration and not limitation, an induced luminescence immunoassay may be employed. The induced luminescence immunoassay is referred to in U.S. Pat. No. 5,340,716 (Ullman), which disclosure is incorporated herein by reference. The assay employs a photosensitizer reagent and a chemiluminescent reagent. In one approach, the assay uses, as a photosensitizer reagent, a label particle-conjugate where the label of the particle-conjugate is a photosensitizer. The chemiluminescent reagent comprises an antibody for the analyte. The analyte competes with the particle-conjugate, which comprises an analyte analog, for the antibody for the analyte. If the analyte is present, the fewer is the number of molecules of labeled particle-conjugate that come into close proximity with the chemiluminescent compound. Therefore, there will be a decrease in the assay signal. The photosensitizer generates singlet oxygen and activates the chemiluminescent reagent when the two labels are in close proximity. The activated chemiluminescent reagent subsequently produces light. The amount of light produced is related to the amount of the complex formed, which in turn is related to the amount of analyte present in the sample.

The concentrations of the various reagents in the assay medium will generally be determined by the concentration range of interest of the analyte, the nature of the assay, and the like. However, the final concentration of each of the reagents is normally determined empirically to optimize the sensitivity of the assay over the range of interest. That is, a variation in concentration of analyte that is of significance should provide an accurately measurable signal difference. Considerations such as the nature of the signal producing system and the nature of the analytes normally determine the concentrations of the various reagents.

As mentioned above, the sample and reagents are provided in combination in the medium. While the order of addition to the medium may be varied, there will be certain preferences for some embodiments of the assay formats described herein. The simplest order of addition, of course, is to add all the materials simultaneously and determine the effect that the assay medium has on the signal as in a homogeneous assay. Alternatively, each of the reagents, or groups of reagents, can be combined sequentially. In some embodiments, an incubation step may be involved subsequent to each addition as discussed below. In heterogeneous assays, washing steps may also be employed after one or more incubation steps.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out an assay and usually constant temperature, preferably, room temperature, during the period of the measurement. Incubation temperatures normally range from about 5° to about 99° C., or from about 15° C. to about 70° C., or about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The time period depends on the temperature of the medium and the rate of binding of the various reagents. Temperatures during measurements will generally range from about 10° C. to about 50° C. or from about 15° C. to about 40° C., for example.

In a next step of an assay method, the medium is examined for the presence of a complex comprising the analyte and antibody for the analyte. The amount of the complex indicates the amount of the analyte in the sample. In many embodiments the examination of the medium involves detection of a signal from the medium. The amount of the signal is related to the presence and/or amount of the analyte in the sample. The particular mode of detection depends on the nature of the sps. As discussed above, there are numerous methods by which a label of an sps can produce a signal detectable by external means. Activation of a signal producing system depends on the nature of the signal producing system members.

Temperatures during measurements generally range from about 10° C. to about 70° C. or from about 20° C. to about 45° C., or about 20° C. to about 25° C. In one approach standard curves are formed using known concentrations of the analyte. Calibrators and other controls may also be used.

Luminescence or light produced from any label can be measured visually, photographically, actinometrically, spectrophotometrically, such as by using a photomultiplier or a photodiode, or by any other convenient means to determine the amount thereof, which is related to the amount of analyte in the medium. The examination for presence and/or amount of the signal also includes the detection of the signal, which is generally merely a step in which the signal is read. The signal is normally read using an instrument, the nature of which depends on the nature of the signal. The instrument may be, but is not limited to, a spectrophotometer, fluorometer, absorption spectrometer, luminometer, and chemiluminometer, for example.

As mentioned above, for the predetermination of the correction factor, the concentration of the hydrophobic haptenic analyte in a sample is conducted on a portion of the sample by a first assay method and on a portion of the same sample by a reference method. These determinations are carried out for each of the samples that are employed in the predetermination of the correction formula in accordance with the principles described herein. The reference method is a method for determination of an analyte that is different from the first assay method employed in the measurement of the concentrations of the hydrophobic haptenic analyte in each of the different samples as discussed above. The reference method should be one that directly measures a character specific to the analyte or its derivatives, for example, the m/z ratio as measured by a mass spectrometric method. Examples of reference methods that may be employed include, by way of illustration and not limitation, mass spectrometry, liquid chromatography including high performance liquid chromatography, for example, electrophoresis, microfluidics, microscopy, spectroscopy, chemical assays, immunoassays, and a combination of two or more thereof.

Once the concentrations of hydrophobic haptenic analyte have been measured by at least the first assay method and the reference method for each of the different samples employed, a bias between the first assay method and the reference method is determined. The bias is the difference between the concentration of the hydrophobic haptenic analyte determined by the reference method and the first assay method for each of the different samples containing the hydrophobic analyte.

In addition to the measurement of the concentrations of hydrophobic haptenic analyte using the first assay method and the reference method in each of the different samples, measurements are also carried out for the concentration of interfering substance in each of the different samples. Measurement of the concentrations of the interfering substance in the different samples may be carried out using an assay method for determining the interfering substance. The assay method may be chosen from any of the first assay methods or reference methods mentioned above. The different samples analyzed should cover a wide range of concentrations of interfering substance so that the correction formula generated in accordance with the principles described herein can be employed for later analysis of a wide range of concentrations of interfering substance encountered for a large patient population. This may be achieved, for example, by analyzing a number of samples in excess of the number necessary for generating the correction formula (see discussion above for the number of samples containing hydrophobic haptenic analyte that are used for generating the correction formula) and selecting, from the samples, those samples that provide for a wide range for concentration of interfering substance.

The correction formula is determined by conducting a regression analysis using the bias and the concentration of the interfering substance in each of the different samples. The regression analysis is one that focuses on the relationship between a dependent variable and one or more independent variables. Any suitable regression analysis may be employed such as, but not limited to, linear regression analysis, high order of polynomial regression, ordinary least squares regression, Passing-Bablok regression, and Deming regression (either weighted or non-weighted), for example.

In an example by way of illustration and not limitation, the regression analysis comprises forming a regression line as in linear regression and developing a correction formula from the slope and intercept of the regression line. In this example, for each different sample the bias obtained as described above is plotted against the concentration of the interfering substance obtained as described above. The following relationship or correction formula may be developed: [An]=[mAn]+(a×[mIS]+b) wherein [An] is the actual concentration of the hydrophobic analyte in the unknown sample, [mAn] is the measured concentration of the hydrophobic analyte in an unknown sample, [mIS] is the measured concentration of the interfering substance in the unknown sample, a is the slope of the regression line, and b is the intercept of the regression line. Therefore, a user such as a laboratory can use the above correction formula to accurately determine the concentration of a hydrophobic haptenic analyte using the assay for which the correction formula was predetermined. After performing the assay, the measured concentration of the hydrophobic haptenic analyte and the measured concentration of the interfering substance in the unknown sample are inserted into the formula to obtain the accurate concentration of hydrophobic haptenic analyte in the unknown sample. For example, for a particular assay for a particular hydrophobic haptenic analyte, the predetermined correction formula was determined to be [An]=[mAn]+(0.22×[mIS]+(−28)); thus, if the value of [mAn] is 36 ng/mL and the value of [mIS] is 130 ng/mL, the equation becomes [An]=36+(0.22×130+(−28)) or [An]=36+28.6−28=36.6 ng/mL.

Kits for Conducting Assays

The reagents for conducting a particular assay may be present in a kit useful for conveniently performing an assay for the determination of a hydrophobic haptenic analyte. In one example, a kit comprises in packaged combination reagents for analyzing for an analyte, the nature of which depend upon the particular assay format. The reagents may include, for example, a binding partner for the analyte. The reagents may each be in separate containers or various reagents can be combined in one or more containers depending on the cross-reactivity and stability of the reagents. The kit can further include other separately packaged reagents for conducting an assay such as additional binding members and ancillary reagents.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay. The kit can further include a written description of a method or assay as well as a correction formula in accordance with the present embodiments as described above.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The designation "first" and "second" is completely arbitrary and is not meant to suggest any order or ranking among the items identified or any order of addition of the items. Examples of the use of first and second herein include, for example, first assay method and second assay method and first sps member and second sps member.

The following examples further describe the specific embodiments of the invention by way of illustration and not limitation and are intended to describe and not to limit the scope of the invention. Parts and percentages disclosed herein are by volume unless otherwise indicated.

EXAMPLES

Determination of Correction Formula

A set consisting of 11 different serum samples was employed wherein each member of the set of samples was obtained from different individuals. A portion of each sample was analyzed for concentration of 25(OH) vitamin D using an immunoassay from Siemens Healthcare Diagnostics Inc. (Newark Del.). The immunoassay was performed on the DIMENSION® clinical chemistry system (Siemens Healthcare Diagnostics Inc.). The DIMENSION® EXL® 25(OH) Vitamin D Total assay (VitD) is a homogeneous competitive chemiluminescent immunoassay based on luminescent oxygen channeling immunoassay (LOCI) technology. It measures the total 25(OH) vitamin D concentration (25(OH) $D_2$ and 25(OH) $D_3$) in both serum and plasma. The LOCI VitD components include a releasing reagent, two synthetic bead reagents and a biotinylated monoclonal antibody. The first bead reagent (Sensibeads) was coated with streptavidin and contained a photosensitive dye and was prepared using a method analogous to that described in U.S. Pat. Nos. 6,153,442, 7,022,529, 7,229,842 and U.S. Patent Application Publication No. 20050118727A. The photosensitizer was bis-(trihexyl)-silicon-t-butyl-phthalocyanine. The second bead reagent (Chemibeads) was coated with a 25(OH) vitamin $D_3$ analog and contained a chemiluminescent dye and was prepared by a procedure similar to that described in U.S. Pat. No. 7,179,660. The chemiluminescent compound was 2-(4-(N,N, di-tetradecyl)-anilino-3-phenyl thioxene with europium chelate. The sample was incubated with a releasing reagent (anilinonaphthalene sulfonic acids (ANS)) to release vitamin D molecules from their binding proteins. The reaction mixture was then incubated with biotinylated antibody to form a 25(OH) vitamin D/biotinylated antibody complex. Chemibeads were added to remove the excess free biotinylated antibody, and then Sensibeads were added to trigger the formation of Chemibead-analog/antibody-biotin/streptavidin-S ensibeads complexes. Illumination of the reaction mixture at 680 nm generated singlet oxygen from the Sensibeads, which diffused into the Chemibeads and triggered a chemiluminescent reaction. The resulting signal was measured at 612 nm and was inversely proportional to the concentration of total 25(OH) vitamin D in the sample.

Another portion of each sample was analyzed for vitamin D concentration using ID-LC/MS/MS isotope-dilution liquid chromatography/mass spectrometry/mass spectrometry) as a reference method.

Another portion of each sample was analyzed for cholesterol concentration by means of a total cholesterol concentration assay (No. DF27) from Siemens Healthcare Diagnostics Inc. according to the manufacturer's protocol. In the assay cholesterol esterase (CE) catalyzes the hydrolysis of cholesterol esters to produce free cholesterol which, along with preexisting free cholesterol, is oxidized in a reaction catalyzed by cholesterol oxidase (CO) to form cholest-4-ene-3-one and hydrogen peroxide. In the presence of horseradish peroxidase (HPO), the hydrogen peroxide thus formed is used to oxidize N,N-diethylaniline-HCl/4-aminoantipyrine (DEA-HCl/AAP) to produce a chromophore that absorbs at 540 nm. The absorbance due to oxidized DEA-HCl/AAP is directly proportional to the total cholesterol concentration and is measured using a polychromatic (452 nm, 540 nm, 700 nm) endpoint technique (nm is nanometers).

Figure 1:
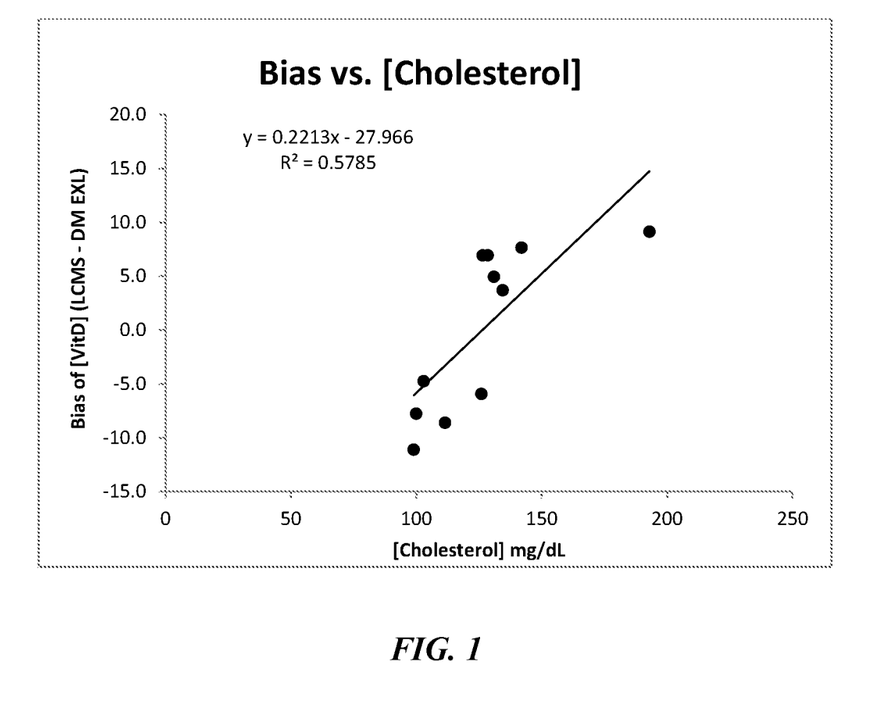
FIG. 1 is a graph depicting bias (obtained by subtracting results of a liquid chromatography-mass spectrometry (LCMS) assay for vitamin D on a set of samples from results of an immunoassay for vitamin D on the same set of samples) plotted against the cholesterol concentration for each member of the set of samples.

The concentration of vitamin D obtained for each different sample using the immunoassay method was subtracted from the concentration of vitamin D obtained for each different sample using the reference method to obtain a bias for each different sample. The bias for each different sample was plotted against the cholesterol concentration for each different sample. The results are depicted in FIG. 1 where [vitD] is the concentration of vitamin D, LCMS is the concentration of vitamin D measured using the reference method, DM EXL is the concentration of vitamin D measured using the immunoassay, mg is milligram, dL is deciliter, y is the criterion variable, x is the predictor variable, and $R^2$ is the square of the correlation coefficient.

From the above results the following correction formula was developed: [An]=[mAn]+(a×[mIS]+b) wherein [An] is the actual concentration of the vitamin D in an unknown sample, [mAn] is the measured concentration of the vitamin D in an unknown sample, [mIS] is the measured concentration of cholesterol in the unknown sample, a is the slope of the regression line, which in this example is 0.2213, and b is the intercept of the regression line, which in this example is −27.966. The correction formula is, therefore, [actual vitamin D]=[measured vitamin D]+(0.2213×[cholesterol]−27.966).

Verification of Correction Formula

Figure 2:
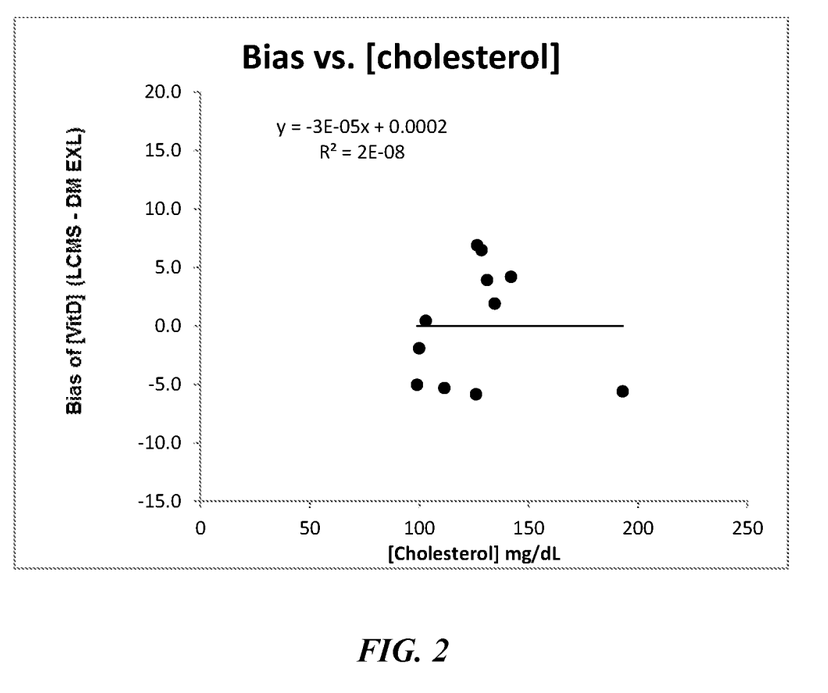
FIG. 2 is a graph depicting the bias of FIG. 1 (corrected based on the correction formula obtained) plotted against the cholesterol concentration for each member of the set of samples.

Verification of the above-determined correction formula was carried out by calculating a bias with an actual concentration of vitamin D using the measured concentration of vitamin D and the above correction formula. The bias was plotted against the cholesterol concentration for each of the different samples. The results are depicted in FIG. 2 where 3E-5 is $3\times10^{-5}$. As can be seen, a correlation between the bias and the cholesterol concentration no longer exists after application of the correction formula to determine an actual concentration of vitamin D in the samples.

Figure 3:
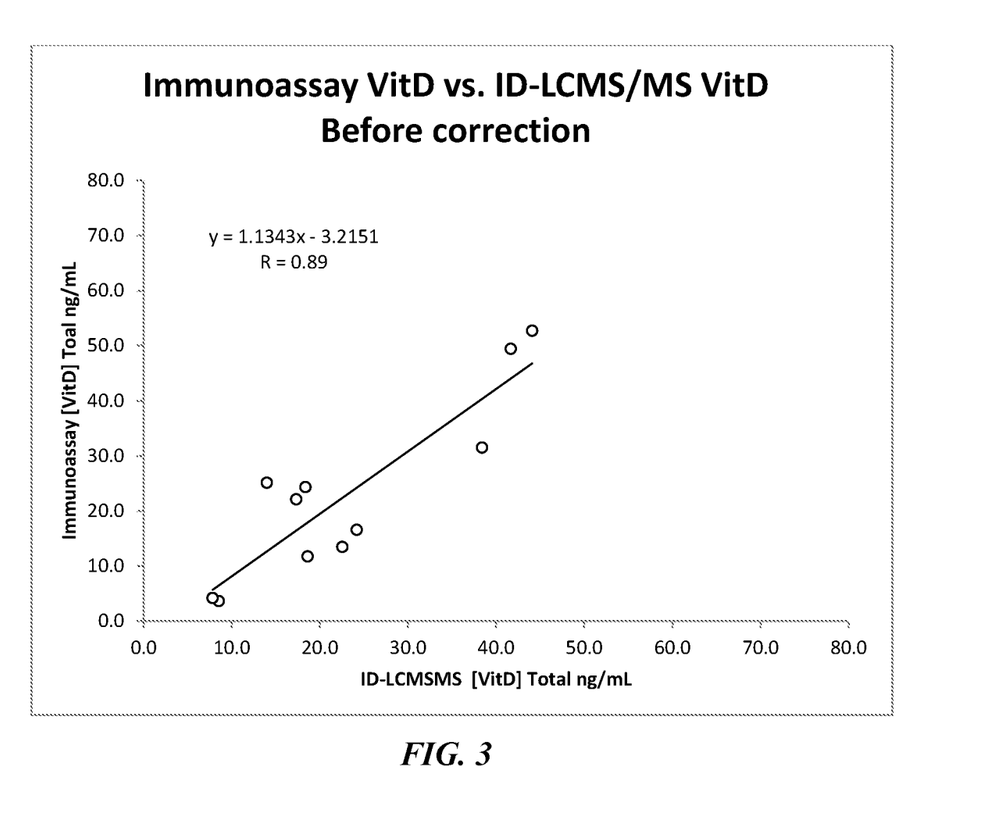
FIG. 3 is a graph depicting the concentration of vitamin D measured by the immunoassay (without application of the correction formula) plotted against the concentration of vitamin D measured by the reference method.
Figure 4:
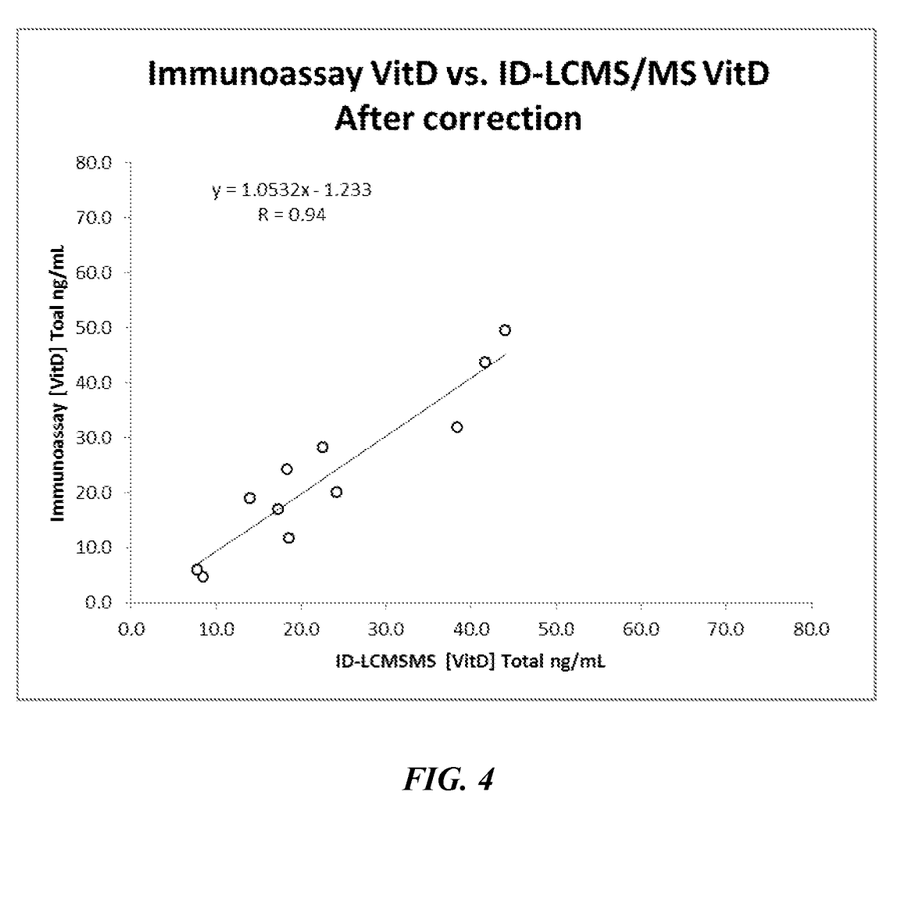
FIG. 4 is a graph depicting the concentration of vitamin D measured by the immunoassay (with application of the correction formula) plotted against the concentration of vitamin D measured by the reference method.

As can be seen with reference to FIGS. 3 and 4, after application of the correction formula, the correlation coefficient (scatter of data in correlation between the vitamin D concentration determined using the immunoassay and the vitamin D concentration determined using the ID-LCMS/MS method) improved. In FIGS. 3 and 4, R is the correlation coefficient, ng is nanogram(s) and mL is milliliter(s).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method of determining an actual concentration of a hydrophobic haptenic analyte in an unknown sample suspected of containing the hydrophobic haptenic analyte, wherein the unknown sample is suspected of containing an interfering substance, the method comprising:
   (a) conducting a first assay method on an unknown sample to obtain a measured concentration of the hydrophobic haptenic analyte in the unknown sample and conducting a second assay method on the unknown sample to obtain a concentration of the interfering substance in the unknown sample, wherein the hydrophobic haptenic analyte is selected from the group consisting of fat-soluble vitamins, steroid hormones, therapeutic drugs, and drugs of abuse, and wherein the interfering substance is lipoproteins; and
   (b) applying a predetermined correction formula that utilizes the measured concentration of the hydrophobic haptenic analyte and the measured concentration of the interfering substance obtained in step (a) to determine an actual concentration of the hydrophobic haptenic analyte in the unknown sample, wherein the correction formula is predetermined by a method that comprises:
   (i) measuring a concentration of the hydrophobic haptenic analyte for at least two different samples using the first assay method and measuring the concentration of the hydrophobic haptenic analyte for the at least two different samples using a reference method wherein the samples also comprise the interfering substance,
   (ii) determining a bias between the first assay method and the reference method wherein the bias is the difference between the concentration of the hydrophobic haptenic analyte determined by the reference method and the first assay method for each different sample;
   (iii) measuring a concentration of the interfering substance for the at least two different samples; and
   (iv) determining the correction formula by conducting a regression analysis using the bias and the concentration of the interfering substance for each of the at least two different samples,
wherein the regression analysis comprises forming a regression line and using the slope and intercept of the regression line to form the following correction formula:

$$[An] = [mAn] + (a \times [mIS] + b)$$

wherein:
   [An] is the actual concentration of the hydrophobic haptenic analyte in the unknown sample,
   [mAn] is the measured concentration of the hydrophobic haptenic analyte in the unknown sample,
   [mIS] is the measured concentration of the interfering substance in the unknown sample,
   a is the slope of the regression line, and
   b is the intercept of the regression line; wherein the first assay method is an immunoassay method and wherein the reference method directly measures a character specific to the analyte and is different from the first assay method.

2. The method according to claim 1 wherein the first assay method comprises:
   (i) adding reagents for determining the measured concentration of the hydrophobic haptenic analyte in the sample to a medium comprising the sample wherein the reagents comprise at least one binding partner for the hydrophobic haptenic analyte, and
   (ii) incubating the medium under conditions for binding of the hydrophobic haptenic analyte to the binding partner for the hydrophobic haptenic analyte.

3. The method according to claim 1 wherein the hydrophobic haptenic analyte is vitamin D.

4. The method according to claim 1 wherein the sample is a body excretion, body aspirant, body excisant or body extractant.

5. The method according to claim 1 wherein the reference method is selected from the group consisting of mass spectrometry, liquid chromatography, electrophoresis, microfluidics, microscopy, spectroscopy, chemical assays and a combination of two or more thereof.

6. The method according to claim 1 wherein the regression analysis comprises forming a regression line and developing the correction formula from the regression line.

7. The method according to claim 1 wherein the first assay method comprises:
   combining in an assay medium the sample with (i) an antibody for the hydrophobic haptenic analyte capable of binding to the hydrophobic haptenic analyte to form complexes and (ii) a member of a signal producing system that produces a signal in relation to the amount of hydrophobic haptenic analyte complexes wherein the member of the signal producing system is bound to the antibody or to a hydrophobic haptenic analyte analog that competes with the hydrophobic haptenic analyte in the sample for binding to the antibody,
   incubating the assay medium under conditions for forming the complexes,
   determining an amount of signal from the complexes, and
   relating the amount of signal to the measured concentration of hydrophobic haptenic analyte in the sample.

8. A method of determining an actual concentration of a vitamin D analyte in an unknown sample suspected of containing the vitamin D analyte, wherein the unknown sample is suspected of containing cholesterol, the method comprising:
   (a) conducting a first assay method on an unknown sample to obtain a measured concentration of the vitamin D analyte in the unknown sample and conducting a second assay method on the unknown sample to obtain a concentration of cholesterol; and
   (b) applying a predetermined correction formula that utilizes the measured concentration of the vitamin D analyte and the measured concentration of cholesterol obtained in step (a) to determine an actual concentration of the vitamin D analyte in the unknown sample, wherein the correction formula is predetermined by a method that comprises:
(i) measuring a concentration of the vitamin D analyte for at least two different samples using the first assay method and measuring the concentration of the vitamin D analyte for the at least two different samples using a reference method wherein the at least two different samples further comprise cholesterol,
(ii) determining a bias between the first assay method and the reference method wherein the bias is the difference between the concentration of the vitamin D analyte determined by the reference method and the first assay method for each different sample;
(iii) measuring a concentration of cholesterol for each of the at least two different samples; and
(iv) determining the correction formula by conducting a regression analysis using the bias and the concentration of cholesterol for each of the at least two different samples, wherein the regression analysis comprises forming a regression line and using the slope and intercept of the regression line to form the following correction formula:

[vitamin$D$]=[$m$ vitamin$D$]+($a$ +[$m$ cholesterol]+$b$)

wherein:
[vitamin D] is the actual concentration of the vitamin D analyte in the unknown sample,
[m vitamin D] is the measured concentration of the vitamin D analyte in the unknown sample,
[m cholesterol] is the measured concentration of cholesterol in the unknown sample,
a is the slope of the regression line, and
b is the intercept of the regression line; wherein the first assay method is an immunoassay method and wherein the reference method directly measures a character specific to the analyte and is different from the first assay method.

9. The method according to claim 8 wherein the first assay method comprises:
(i) adding reagents for determining the measured concentration of the vitamin D analyte in the sample to a medium comprising the sample wherein the reagents comprise at least one binding partner for the vitamin D analyte, and
(ii) incubating the medium under conditions for binding of the vitamin D analyte to the binding partner for the vitamin D analyte.

10. The method according to claim 8 wherein the sample is a body excretion, body aspirant, body excisant or body extractant.

11. The method according to claim 8 wherein the reference method is selected from the group consisting of mass spectrometry, liquid chromatography, electrophoresis, microfluidics, microscopy, spectroscopy, chemical assays, and a combination of two or more thereof.

12. The method according to claim 8 wherein the regression analysis comprises forming a regression line and developing the correction formula from the regression line.

13. The method according to claim 8 wherein the first assay method comprises:
combining in an assay medium the sample with (i) an antibody for the vitamin D analyte capable of binding to the vitamin D analyte to form complexes and (ii) a member of a signal producing system that produces a signal in relation to the amount of vitamin D analyte complexes wherein the member of the signal producing system is bound to the antibody or to a vitamin D analyte analog that competes with the vitamin D analyte in the sample for binding to the antibody,
incubating the assay medium under conditions for forming the complexes,
determining an amount of signal from the complexes, and
relating the amount of signal to a measured concentration of vitamin D analyte in the sample.

* * * * *